US005560819A

United States Patent [19]

Taguchi

[11] Patent Number: 5,560,819

[45] Date of Patent: Oct. 1, 1996

[54] TREATING SYSTEM FOR ORGANIC WASTES AND WASTE WATER

[75] Inventor: Akira Taguchi, 8-14, Kamikosaka 2-chome, Higashiosaka-shi, Osaka 577, Japan

[73] Assignees: Mori-Gumi Co., Ltd.; Akira Taguchi, both of Japan

[21] Appl. No.: 396,069

[22] Filed: Feb. 28, 1995

Related U.S. Application Data

[63] Continuation of Ser. No. 164,770, Dec. 10, 1993, abandoned, which is a continuation of Ser. No. 934,486, filed as PCT/JP91/00515, Apr. 18, 1991, published as WO91/16268, Oct. 31, 1991, abandoned.

[30] Foreign Application Priority Data

Apr. 19, 1990 [JP] Japan ..................... 2-103700
Apr. 18, 1991 [WO] WIPO ............... PCT/JP91/00515

[51] Int. Cl.⁶ ............................................... C02F 3/28
[52] U.S. Cl. ................. 210/104; 210/120; 210/150; 210/188; 210/603; 210/615
[58] Field of Search ........................ 210/104, 120, 210/150, 151, 188, 336, 603, 615, 617

[56] References Cited

U.S. PATENT DOCUMENTS

| | | | |
|---|---|---|---|
| 2,188,162 | 1/1940 | Schulhoff | 210/150 |
| 4,294,694 | 10/1981 | Coulthard | 210/150 |
| 4,303,528 | 12/1981 | Shibayama | 210/615 |
| 4,599,168 | 7/1986 | Benjes et al. | 210/151 |
| 4,620,929 | 11/1986 | Hofmann | 210/617 |
| 4,680,111 | 7/1987 | Ueda | 210/150 |
| 4,696,747 | 9/1987 | Verstraete et al. | 210/617 |
| 4,717,519 | 1/1988 | Sagami | 210/150 |
| 4,780,415 | 10/1988 | Ducellier et al. | 210/603 |
| 4,925,552 | 5/1990 | Bateson et al. | 210/617 |

FOREIGN PATENT DOCUMENTS

| | | |
|---|---|---|
| 59-32915 | 2/1984 | Japan . |
| 60-244396 | 12/1985 | Japan . |
| 61-158786 | 7/1986 | Japan . |
| 644300 | 1/1989 | Japan . |

*Primary Examiner*—Christopher Upton
*Attorney, Agent, or Firm*—Wenderoth, Lind & Ponack

[57] ABSTRACT

A treating system comprising a horizontal zigzag flow or vertical zigzag flow treating tank having a plurality of chambers constituted by horizontally or vertically dividing the inside of the tank by partitions and connected to one another in a horizontal or vertical zigzag fashion and having filter media installed in each chamber in a standing or lying position, or a treating system having independent chambers connected with one another where treating substances flow in an alternate fashion of downward and upward flows and is discharged from the last chamber and having filter media installed in each chamber in a standing position, said filter medium comprising a core element and a number of thin tapes of synthetic resin extending radially around the core element.

The treating efficiency of the system may be increased by connecting an automatic gas-lift stirring device which performs stirring of the contents of the treating tank using methane gas generating in the treating tank.

3 Claims, 11 Drawing Sheets

TREATING SYSTEM FOR ORGANIC WASTES AND WASTE WATER

This application is a continuation of now abandoned application Ser. No. 08/164,770, filed Dec. 10, 1993; which is a continuation of now abandoned application Ser. No. 07/934,486, filed Sep. 15, 1992; which is the U.S. National Stage of PCT/JP91/00515, filed Apr. 18, 1991 and published as WO91/16268 Oct. 31, 1991.

TECHNICAL FIELD

This invention relates to an improvement of a treating system for treating such organic wastes and liquid waste as excrement, kitchen garbage and organic industrial liquid waste, and more particularly, to an improvement of a methane fermentation tank for treating organic solid or liquid waste utilizing methane fermentation, filter media and an stirring device for stirring the inside of the tank.

BACKGROUND ART

There have been many developments in the field of anaerobic treatment of organic solid and liquid waste, including a simple single-tank system requiring 20 to 40 days for the completion of treatment, a double-tank system with higher treatment efficiency, a system using a fixed or fluid filtering bed, a system wherein bacteria accumulate in large quantities in a reaction tank in a granular or integrated solid form, which has drastically increased treatment efficiency, and a system wherein bacteria are allowed to float and multiply so that their fissiparous membranes are utilized. The efficiency of anaerobic treatment has thus increased remarkably.

However, systems of high efficiency are generally limited to treatment of specific organic matter. It is also considered difficult in general to treat organic matter in low content, and in many cases, advanced techniques are required for the adaptation of bacteria to the systems and for their successful operation.

DISCLOSURE OF INVENTION

It is therefore an object of the present invention to provide a simple and highly efficient treating system for the treatment of organic solid and liquid waste which is capable of treating not only specific organic waste of high content but a wide range of various organic waste, including home waste water containing organic substances of low content, urban sewage, combined sewage (mixture of liquid waste consisting of flush toilet sewage and home waste water), home solid waste such as leftover food and other food waste, waste water mixed with disposal-processed garbage, human waste, and livestock and industrial waste water.

The inventor of this invention has previously provided in the Patent application laid open under Ser. No. 64-4300 a treating system for organic solid and liquid waste to attain similar objects. The present invention attempts to improve said treating system, treating tank used in said system, filter media used in said tank and automatic gas-lift stirring device used to stir contents in the treating tank, so that anaerobic treatment is accomplished with higher efficiency.

There are three types of embodiments of the treating tank to be used in the treating system in accordance with the present invention, that is, a horizontal zigzag flow tank, a vertical zigzag flow tank and a vertical alternate flow tank.

The horizontal zigzag flow tank comprises a sloped bottom and a plurality of chambers made by dividing the tank horizontally with partitions and connected to one another in a horizontal zigzag fashion. The waste to be treated enters the tank from an upper end of the slope and treated waste emerges from a lower end of the slope. Each chamber is filled with filter media placed in a standing position.

The vertical zigzag flow tank comprises a plurality of chambers made by vertically dividing the tank with partitions and connected to one another in a vertical zigzag fashion so that treated waste flows parallel to the partitions. Either an upper end or a lower end receives waste to be treated, and the other end discharges treated waste. In each chamber are placed filter media in a lying position.

The vertical alternate flow tank comprises independent chambers connected to each other by connecting tubes so that waste may flow from one chamber to the other, alternately flowing upward and downward, and is discharged from the last chamber through either an upward or downward flow. Each chamber is filled with filter media placed in a standing position.

The filter medium placed in the above chambers comprises a core element and a number of thin tapes of synthetic resin extending radially from the core element.

The treating system using any of the above treating tanks may be made more efficient by installing an automatic gas-lift stirring device. Namely, there is installed an automatic gas-lift stirring device having a gas tank connected through valves to a methane gas outlet provided at an upper portion of the tank and a methane gas inlet provided at the bottom of the tank. Said automatic gas-lift stirring device comprises a water tank which is filled with a prescribed amount of water and is connected to an stirring tower above, a gas chamber having an open bottom and placed in the water tank and a sensor which sends control signals to close a valve in a line to the methane gas outlet and open a valve in a line to the methane gas inlet by sensing when the water rises to a prescribed level in a stirring tower by gas pressure.

Any of the above treating tanks of horizontal zigzag flow type, vertical zigzag flow type and vertical alternate flow type is designed to have the fermentation treatment process take place in orderly fashion, by limiting direct delivery or useless circulation or detouring of the objects to be treated to a minimum and by making the whole process from inflow to discharge as even and as lengthy as practically possible. Thus, treatment efficiency per unit of hydraulic retention time (HRT) naturally increases.

The vertical alternate flow tank having air-tight independent chambers allows of suspension of operation or repair of some chambers even while the rest of the system is in operation, of directional insertion of the vertical flow in each chamber, or of conversion of the chambers to other application such as solid/liquid separation tanks or seeding tanks, by changing the connections of connecting tubes. It is also possible to manufacture each chamber as a standardized component through mass production, which will decrease manufacturing costs and lead to easier transportation, installation and repair.

Numerous filter media comprising a core element and thin tapes of synthetic resin extending radially from the core element are installed in the chambers of the tank in a standing or lying position, so that anaerobic bacteria are stored in large quantities in the tank. Said filter media move in an undulating manner in all directions at varying speeds by the effect of the automatic gas-lift stirring conducted in the tank, and therefore they are closer to fluid-bed rather than fixed bed so that the possibility of clogging is eliminated. Fluid-bed operation requires the maintenance of good fluidity, so that the film of microbial membranes remains thin. The automatic gas-lift stirring controls gas pressure, gas volume and stirring frequency so that excess growth of microbial membranes is controlled to the optimal level. Accordingly the anaerobic treatment of industrial and home organic solid or liquid waste of low, medium or high content can be carried out with high efficiency.

By changing the location of the sensor and increasing or decreasing the amount of water in the water tank and the stirring tower in the automatic gas-lift stirring device, the volume and pressure of gas to be used for stirring and the intensity and frequency of stirring can be adjusted variously, so that optimal operation of the system is allowed in accordance with the amount of gas generated inside the treating tank. When gas generation increases in step with the increase in activity of methane-generating bacteria, the frequency of stirring also increases and thereby the activity of the methane-generating bacteria is accelerated.

When the intensity (gas volume and pressure) and frequency of stirring exceed a peak, separation of the microbial membrane generated at the surface of the filter medium increases and the treatment efficiency drops. However, with this automatic gas-lift stirring, the stirring frequency is automatically reduced as gas generation decreases after this peak and the separation is eliminated so that optimal gas generation is continuously maintained with stirring at the prescribed gas volume and pressure. Therefore, the stirring device is capable of maintaining the optimal level of activity of methane-generating bacteria in the treating tank as well as the optimal level of gas generation.

Accordingly, the treating system using the aforesaid treating tank, and further a treating system equipped with the treating tank and the automatic gas-lift stirring device is a optimal treating system for a wide range of organic solid and liquid waste which performs anaerobic treatment of industrial and home waste of low, medium or high content with high efficiency. In other words, there can be treated various kinds of organic waste, for example, treatment of flush toilet water which contains a relatively low concentration of organic substances, treatment of leftover food and kitchen waste water mixed with disposal-processed garbage which contains a relatively high concentration of organic substances, and treatment of a combination of part or all of these organic waste. It can also shorten the conventional treatment period of 20 to 40 days to one day or so. Adaptation of methane-generating bacteria to this system is easily made, and such problems as clogging and washout are also resolved. Thus the present invention provides the treating system which can perform anaerobic treatment of various organic solid and liquid waste such as domestic, livestock and industrial waste water, regardless of the concentration, type or scale thereof, with easy operation and high efficiency.

BEST MODE FOR CARRYING OUT THE INVENTION

Referring to the attached drawings methane fermentation treatment of organic solid and liquid waste in accordance with the present invention is now described, but a filter medium and treating tank using said filter medium may be also applied to aerobic treating tanks and anaerobic fixed filtering beds.

1. Treating tanks

Figure 1:
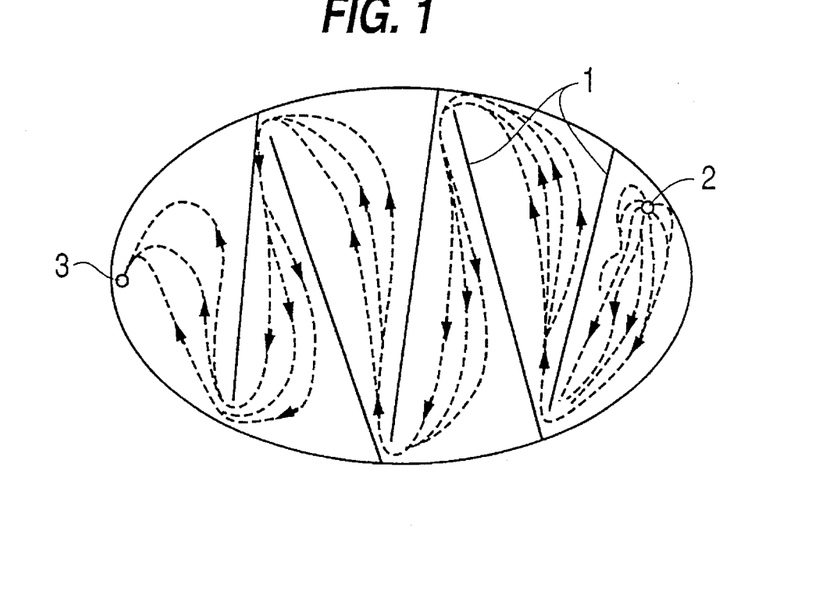
FIG. 1 is a schematic plan view of a horizontal zigzag flow tank showing one embodiment of the treating tank in accordance with the present invention.
Figure 2:
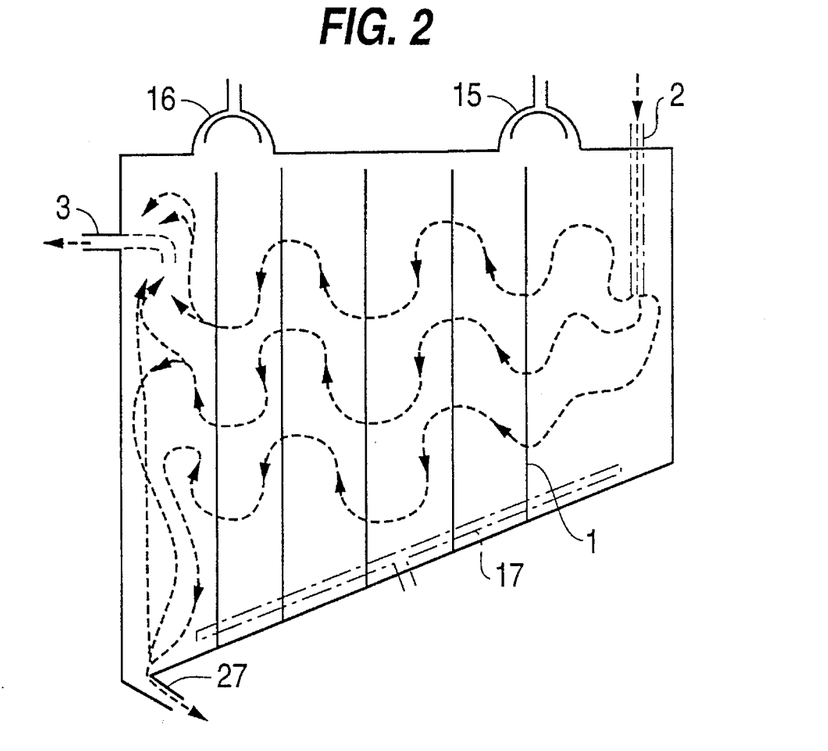
FIG. 2 is a schematic front view of the same.
Figure 3:
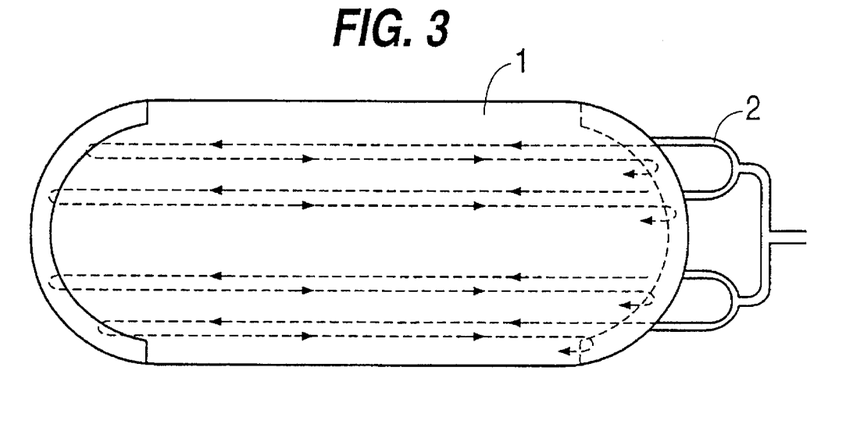
FIG. 3 is a schematic plan view of a vertical zigzag flow tank showing another embodiment of the treating tank in accordance with the present invention.
Figure 4:
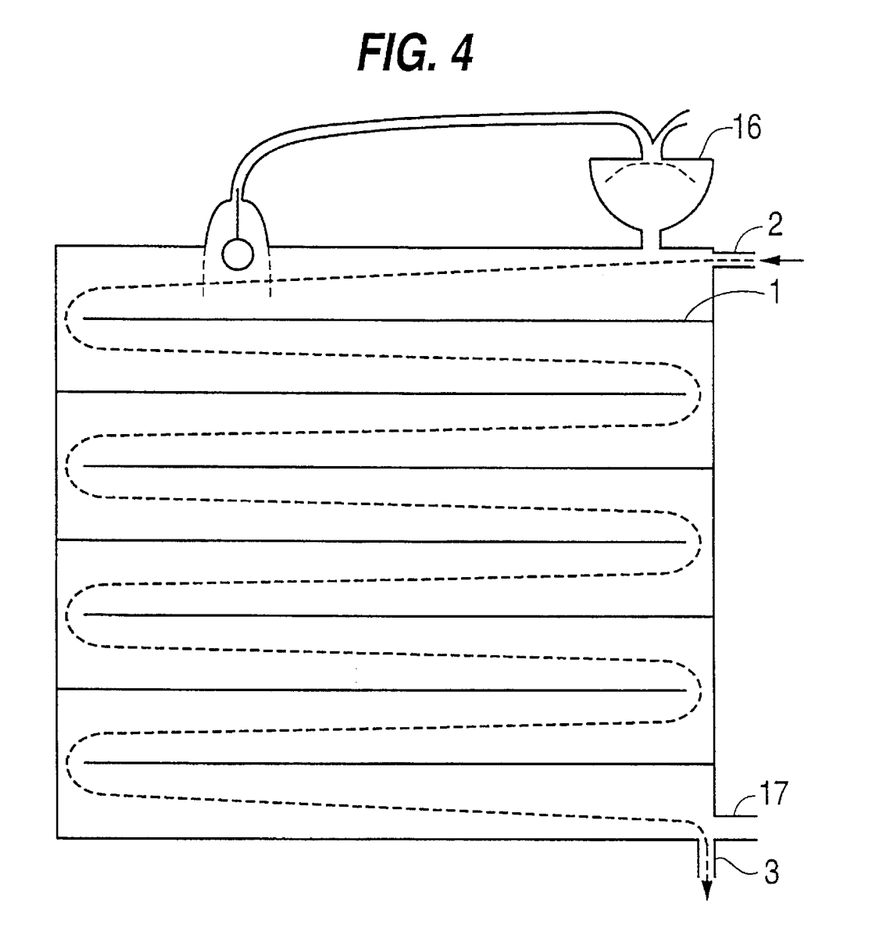
FIG. 4 is a schematic front view of the same.

FIGS. 1 through 6 represents embodiments of the treating tanks in accordance with this invention. FIGS. 1 and 2 show a horizontal zigzag flow tank and FIGS. 3 and 4 show a vertical zigzag flow tank.

Although the tanks are represented as elliptic cylinders in the figures, various shapes including round or rectangular cylinders are employable depending on the location of installation, as far as organic substances are effectively treated in the course of horizontal zigzag flow or vertical zigzag flow inside the tank.

The horizontal zigzag flow tank in FIGS. 1 and 2 has a sloped bottom and six to eight chambers partitioned by five to seven partitions 1. Organic substances introduced through an inlet 2 formed at the upper end of the slope reach the final chamber after completing the treatment process in a horizontal zigzag fashion and are discharged as treated liquid through an outlet 3 formed at the lower end of the slope, as shown in dotted lines.

In the vertical zigzag flow tank shown in FIGS. 3 and 4, organic substances introduced through the inlet 2 reach the final chamber after completing the treatment process in a vertical zigzag fashion from top to bottom along partitions 1 which divides the tank horizontally and are discharged through the outlet 3, as shown in dotted lines.

The number of partitions 1 is not limited. It has been proven that zigzag flow through the minimum two partitions and three chambers shows a considerably high BOD removal rate.

FIGS. 7 through 14 represent a vertical alternate flow tank exemplifying another embodiment of the treating tank according to this invention. FIGS. 7 through 10 show a tank with a hexagonal cylindrical shape and FIGS. 11 through 14 show a tank with a rectangular cylindrical shape. Other cylindrical shapes such as round or pentagonal shapes are also available.

Said tank may be constructed by equally dividing the inside thereof by partitions into six independent air-tight chambers or assembling six independent components of identical size and shape.

In the figures, there is shown by the dotted lines the process in which organic substances urged into the upper part of chamber a through an inlet 2 reach the bottom via downward flow, flow into the bottom of the next chamber b through a connecting tube 4, reach the upper part of chamber b via an upward flow, flow into the upper part of next chamber c through a connecting tube 4, reach the bottom of chamber c via a downward flow, repeating the same alternate upward and downward flows in chambers d, e and f, and reach the upper part of the chamber f and then discharging the treated organic substances are made through an outlet 3. In case the first intake is made from the bottom of the first chamber, the flow in the next chamber becomes a downward flow.

Figure 10:
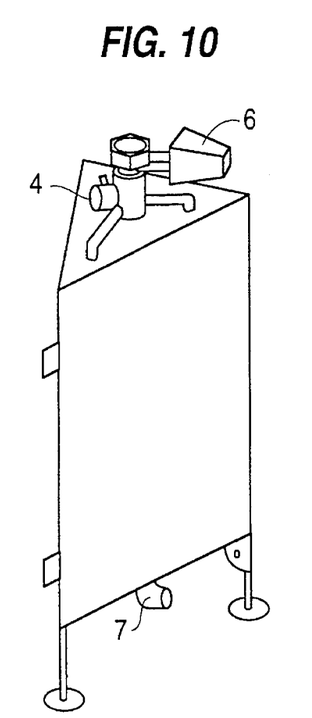
FIG. 10 is a perspective view of a single unit of a vertical alternate flow tank which is assembled with component units.
Figure 11:
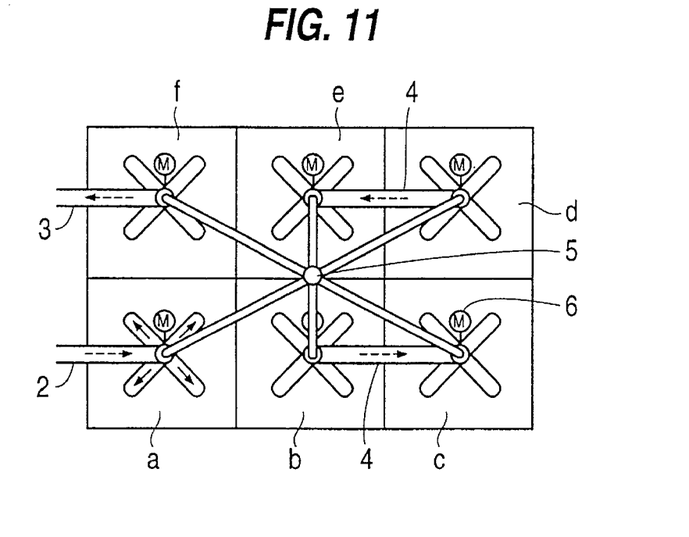
FIG. 11 is a plan view of another embodiment of the vertical alternate flow tank showing a box type.
Figure 12:
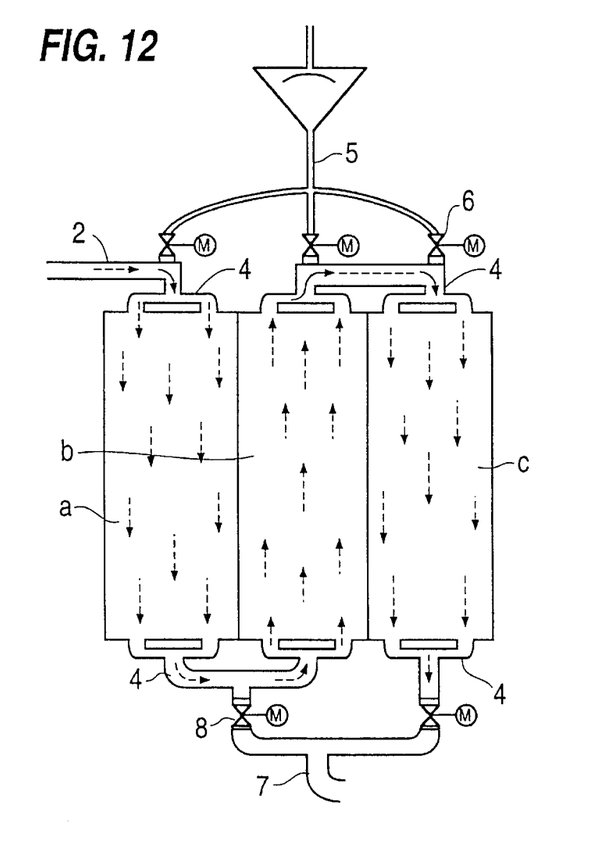
FIG. 12 is a front view of the same.
Figure 13:
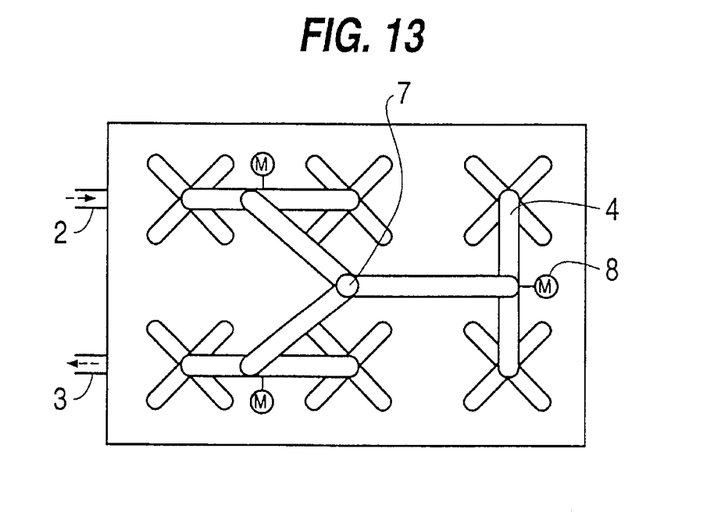
FIG. 13 is a bottom view of the same.
Figure 14:
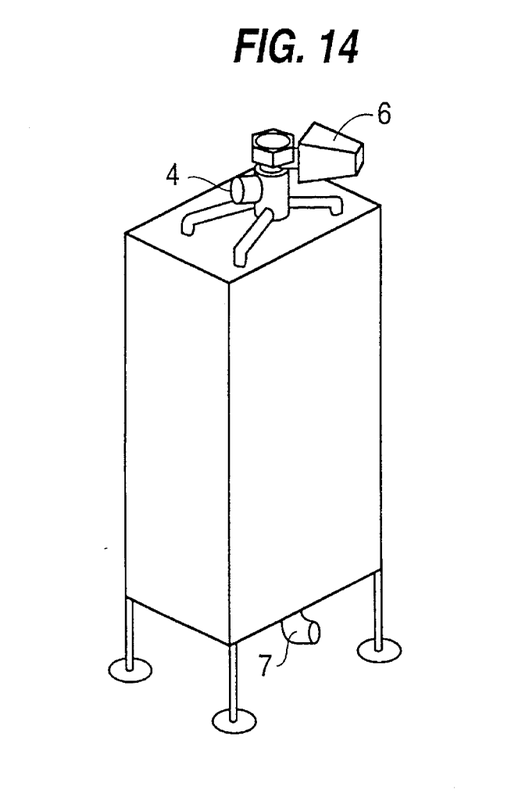
FIG. 14 is a perspective view of a single unit of a vertical alternate flow tank which is assembled with component units.

FIGS. 10 and 14 are perspective diagrams of embodiments of a single unit of an assembly-type treating tank. The unit in FIG. 10 forms a hexagonal cylindrical tank, while the unit in FIG. 14 forms a rectangular cylindrical tank.

In FIG. 7 through 14, 5 is a methane gas outlet connected to each chamber via a motor-driven valve 6, and 7 is an inlet for methane gas used for stirring which is connected with each chamber via a motor-driven valve 8.

Figure 15:
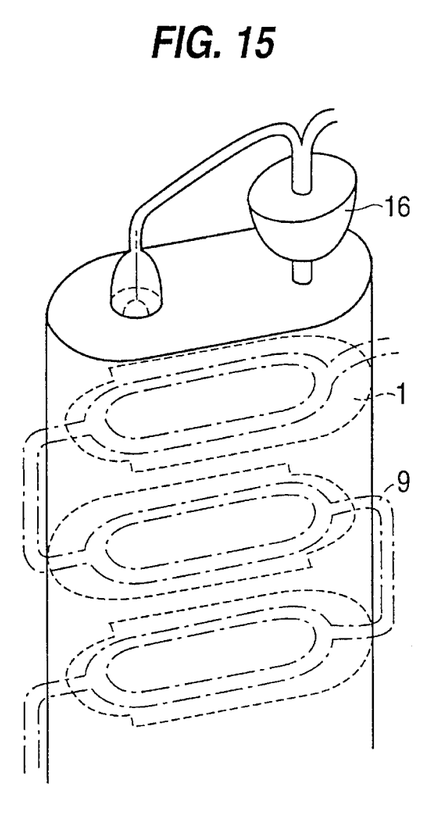
FIG. 15 is a schematic perspective view of the installation of heat exchange pipes connecting to each chamber of the vertical zigzag flow tank.
Figure 16:
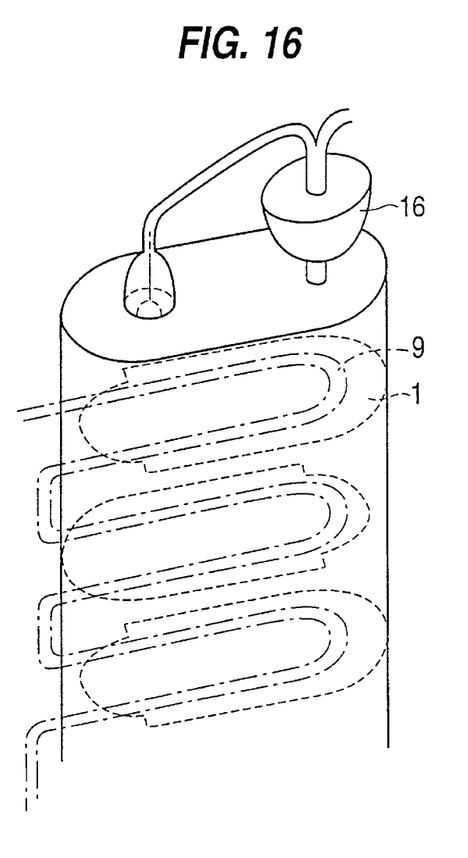
FIG. 16 is a achematic perspective view showing another embodiment of installation of said heat exchange pipes.
Figure 17:
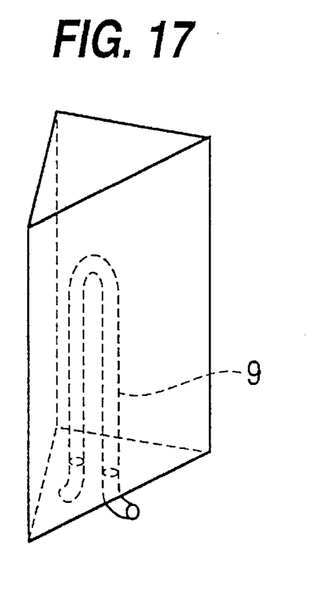
FIG. 17 and FIG. 18 is a perspective view of the installation of heat exchange pipes used with the single unit of the assemble-type treating tank.
Figure 18:
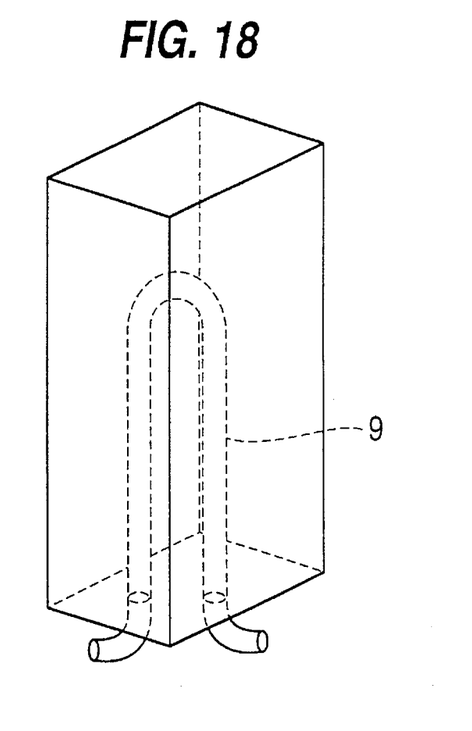

FIGS. 15 and 18 indicate the installation of heat exchange pipes in the tank. Heating of the horizontal zigzag flow tank can be achieved merely by heating the bottom of the tank, as convection can be used for the conduction of heat. But in the case of the vertical zigzag flow tank, as indicated in FIGS. 15 and 16, pipes 9 are installed in each stage and connected to each other in turns via connectors along the side or sides of the tank so that warm water is circulated therein. In the case of the assembly-type tank, as shown in FIGS. 17 and 18, a heat exchange pipe 9 is installed in each unit and connected with each other between adjacent units via connectors so that warm water is circulated therein.

As mentioned above, the treating tank in accordance with this invention, in each of three types of the horizontal zigzag flow tank, the vertical zigzag flow tank and the vertical alternate flow tank, is designed so that the treatment process is carried out in an orderly fashion by limiting the direct delivery, useless circulation or detour of organic substances to a minimum and by making the whole process from the intake to discharge as lengthy as practically possible. Therefore, the treatment efficiency per unit of hydraulic retention time naturally increases. While the reaction rate of a conventional treating tank in a single-tank system is low and is said to take 20 to 40 days to complete the reaction, a horizontal zigzag flow tank with five chambers and four partitions is capable of achieving the same treatment results in five to ten days, a quarter of the time required for the conventional single-tank system, even without installing filter media.

When an experiment was performed with installing filter media as described later, a horizontal zigzag flow tank (with four partitions and five chambers) could accomplish the treatment in one to two days, and the vertical zigzag flow tank could attain higher efficiency.

Since the vertical alternate flow tank is composed of independent air-tight chambers, it is possible to suspend the operation of or perform repairs to some of the chambers during the operation of the system, change the direction of flow in any one chamber, or convert some chambers into different uses, such as solid/liquid separation tanks and seeding tanks, simply by changing the connection of connecting tubes 4. Although this type of tank takes high cost because a large number of motor-driven valves and connecting tubes are required than the horizontal zigzag flow tank or the vertical zigzag flow tank, the reduction of cost may be achieved by standardizing and massproducing the components. This also makes transportation and installation easier, which may compensate for the cost problem.

2. Automatic Gas-Lift Stirring Device

Figure 19:
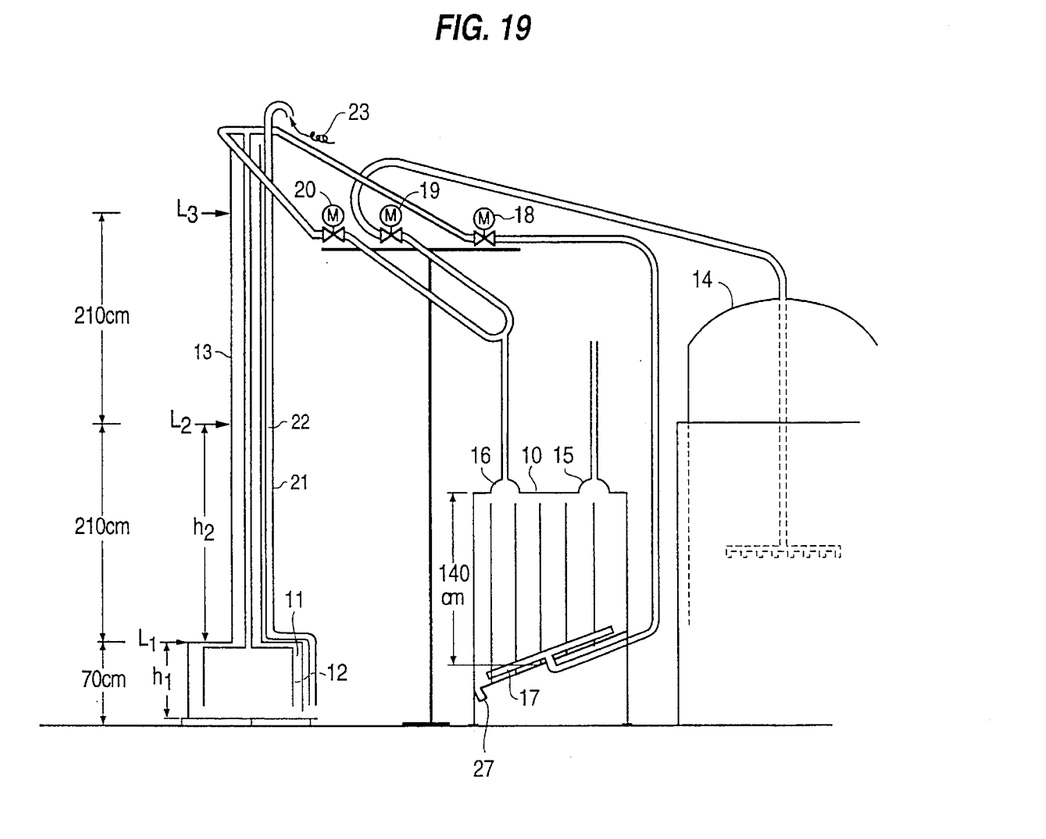
FIG. 19 is a front view of a treating system comprising a horizontal zigzag flow tank, automatic gas-lift stirring device and a gas tank showing one embodiment of the present invention.

FIG. 19 shows an embodiment of the treating system of this invention using one of the above tanks. In this figure, 10 is a horizontal zigzag flow tank with a capacity of 5 m$^3$. The same principle applies to a vertical zigzag flow tank or a vertical alternate flow tank as well. 11 is a water tank having a 1 m$^3$ gas chamber 12 therein, to the top of which an stirring tower 13 is connected. 14 is a water-sealed gas tank.

The methane gas generated in the treating tank 10 gushes through methane gas outlets 15 and 16 provided at the top of the tank at equal pressure. Methane gas outlet 15 is connected to a pressure gauging and a safety device, for example such a device as disclosed in the patent application laid open under Ser. No. 63-235839. Methane gas outlet 16 is connected to an automatic gas-lift stirring device as described below. Methane gas outlet 5 in the vertical alternate flow tank in FIG. 7 through 14 is equivalent to this outlet 16 and is also connected to an automatic gas-lift stirring device. The water-sealed gas tank 14 does not exceed a prescribed gauge pressure. For example, when the gauge pressure is prescribed as being 0 to 0.13 atm, surplus methane gas escapes from the opening between the gas tank and the water tank when the tank is filled with methane gas with 0.13 gauge pressure, and the gauge pressure in the tank does not exceed 0.13 atm.

Figure 5:
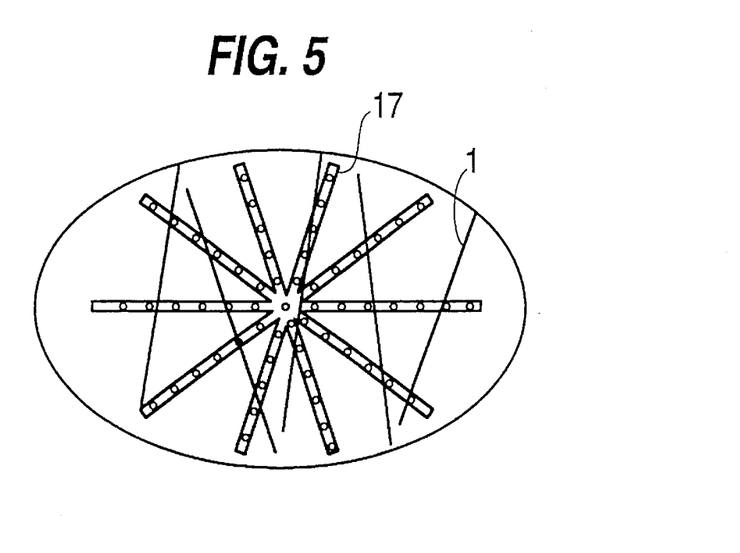
FIG. 5 is a schematic plan view of the installation of gas flow pipes for stirring gas used with the horizontal zigzag flow tank.
Figure 6:
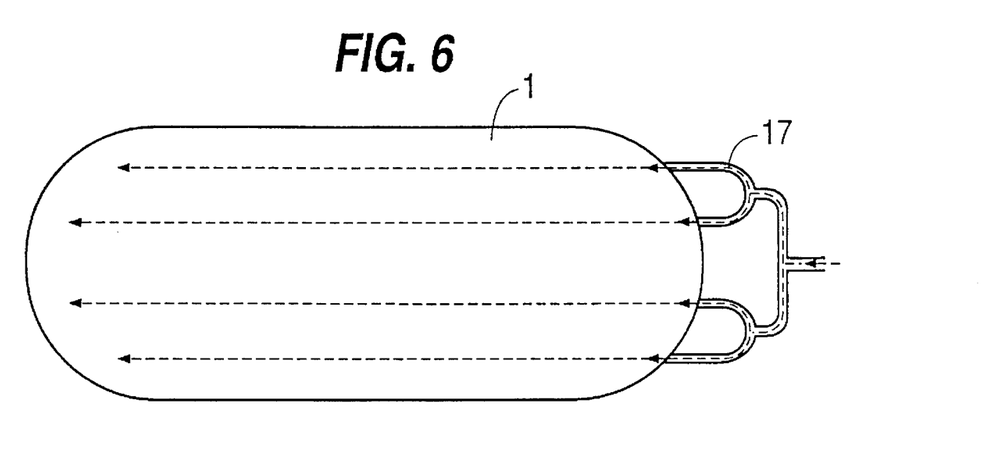
FIG. 6 is a schematic plan view of the installation of gas flow pipes for stirring gas used with the vertical zigzag flow tank.
Figure 7:
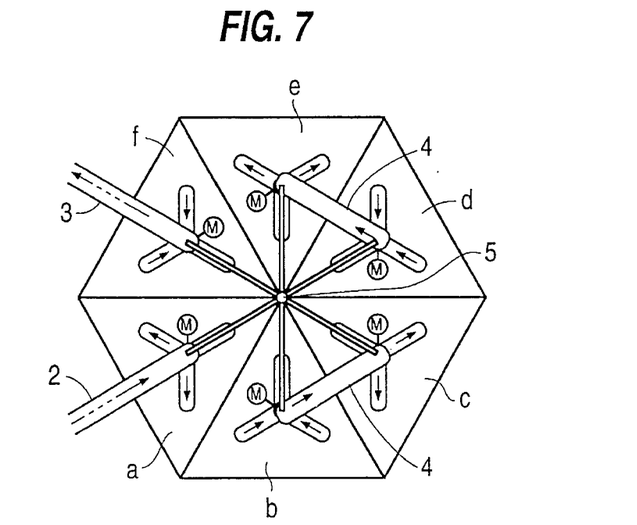
FIG. 7 is a plan view of a vertical alternate flow tank showing another embodiment of the treating tank in accordance with the present invention.
Figure 8:
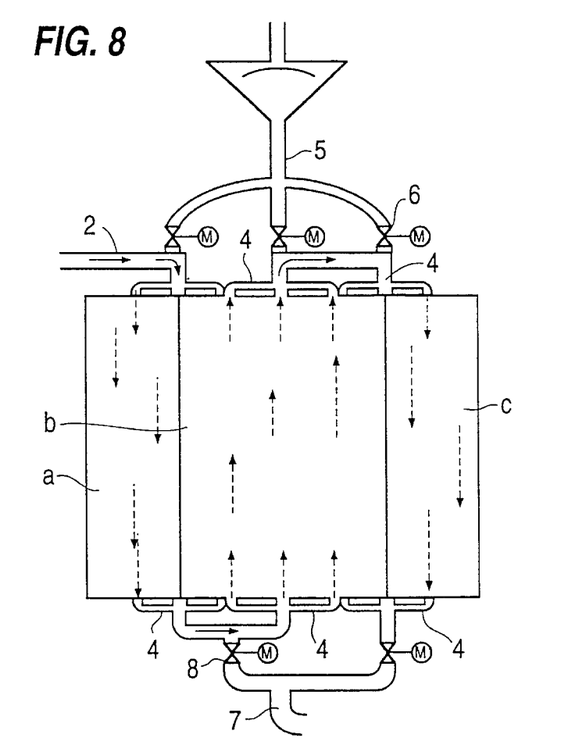
FIG. 8 is a front view of the same.
Figure 9:
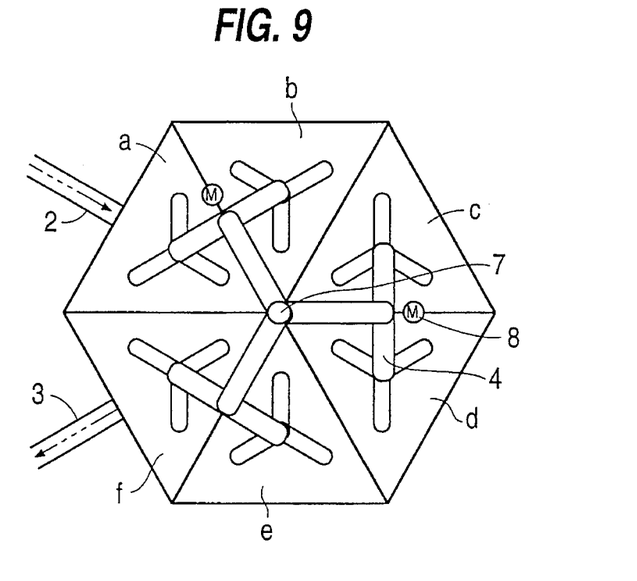
FIG. 9 is a bottom view of the same.

At the bottom of treating tank 10 is attached an intake pipe 17 for the stirring gas. As shown in FIG. 5, this intake pipe has a plurality of branch pipes radially extending at even distances at the bottom of the tank, and each pipe has a number of small holes for blowing the gas into the tank. The number of holes is proportional to the area of the bottom of the tank. In the case of the vertical zigzag flow tank or the vertical alternate flow tank, the number of holes is proportional to the area of the bottom of each chamber or unit. It corresponds roughly to the number of core elements of the filter media or one per 15–30 cm².

Outlet 16 of the treating tank is connected to the stirring tower 13 and the gas tank 14 via three motor-driven valves 18, 19 and 20 for controlling the automatic gas-lift stirring device. As described above, the stirring tower 13 is mounted on the 2 m³ water tank 11 equipped with a 1 m³ gas chamber 12 having the bottom opened. The difference in capacity between water tank 11 and gas chamber 12 is 1 m³ as well. The inner volume of the cylinder extending from point L1 at the bottom to the level L2 of the stirring tower 13 is also 1 m³.

In order to measure the water level in the water tank 11 and the stirring tower 13, a transparent tube 21 having an opening in the vicinity of the tank bottom is installed along the water tank and the stirring tower. A control sensor 22 is inserted into the tube from the upper end thereof to perform automatic gas-lift stirring under various conditions. This sensor is fixed at the level L2. 23 is a lead wire. Since strict precision is not required, the inner volume of the transparent tube will be disregarded below.

When 2 m³ of water (or preferably anti-freeze solution) is poured from the upper end of stirring tower 13, the water fills up the gas chamber 12 as well as the water tank 11 through the open bottom of gas chamber 12, reaching the level $L_1$ which is the bottom level of the stirring tower 13. Methane gas generating in the treating tank 10 rises above and gushes out from the outlet 16. When valve 20 is open among the three motor-driven valves 18, 19 and 20, the gas passes through valve 20 and enters the gas chamber 12, and thereby the water in the gas chamber 12 is expelled and rises through the opening between the water tank and the gas chamber into the stirring tower 13. Since methane gas continues to be generated in the treating tank 10, the volume and pressure of gas inside the gas chamber 12 increases, and thereby the water in the gas chamber rises gradually in the stirring tower 13. When the water level reaches the level $L_2$, the water level in transparent tube 21 reaches the same level as well and the sensor set at that level detects the water surface and sends out signals to be explained below.

When the water level reaches the level $L_1$, the gas chamber 12 is filled with 1 m³ of methane gas and the gauge pressure therein is $(h_1+h_2)$cm/1,000 cm, wherein $h_1$ is the depth of the water tank 11 and $h_2$ is the distance between $L_1$ and $L_2$. In case $h_1$ is 70 cm and $h_2$ is 210 cm, the gauge pressure is 0.28 by 280 cm/1000 cm. The gauge pressure of the methane gas in the treating tank 10 is 0.28 as well.

At the instant that the sensor 23 detects the water at the level $L_1$, a signal is sent out to close the motor-driven valve 20 and open the valves 18 and 19. When the valve 19 is open, the methane gas of 0.28 atm gauge pressure in the treating tank flows out to a gas tank 14 through the motor-driven valve 19 and the pressure in the tank decreases. Since motor-driven valve 18 is open, the 1m₃ gas having 0.28 atm gauge pressure in the gas chamber 12 is led through the pipe via the motor-driven valve 18 to the treating tank and gushes as a stirring gas from a plurality of small holes of the intake pipe 17 branched at the bottom of the treating tank. The gushing gas rises in the treating tank, flowing from side to side and front to back between the filter media spreading full and wide in the tank with the core element in a standing position, thereby causing sufficient stirring, and then leaves the treating tank, flowing into the gas tank 14 via outlet 16 and motor-driven valve 19. The water depth at the bottom of the treating tank acts a pressure against the intake of the stirring gas. Where the water depth is 140 cm, the gauge pressure is 0.14 atm which is higher than the highest gauge pressure, 0.13 atm of the gas tank and the stirring gas no longer flows into the gas tank.

In this embodiment, the water column in the stirring tank 13 falls from a level of 280 cm to 140 cm, reducing the gas pressure from a gauge pressure of 0.28 atm to 0.14 atm. 0.5 m³, that is half of the 1 m³ is used for stirring and the remaining 0.5 m³ remains in the gas chamber 12 with a gauge pressure of 0.14 atm.

When stirring is completed, the motor-driven valve 20 is opened and the valves 18 and 19 is closed receiving signal. The methane gas generating in the treating tank flows again into the gas chamber 12 and raises the water level in the stirring tower 13. Unless the amount of the gas generating in the treating tank changes, the water reaches the level L2 in half the previous time and stirring starts. When the gas in the gas chamber 12 flows into the treating tank via the motor-driven valve 18, thereby performing stirring, and flows into the gas tank 14 via valve 19, the pressure levels in the gas chamber 12 and in the treating tank 10 attain equilibrium. Thereupon immediate reversion is made, that is, the motor-driven valve 20 is opened and the valves 18 and 19 are closed, and thereby the gas begins to accumulate again in the gas chamber 12 so that the preparation for yet another stirring is made. To artificially reduce the frequency of stirring, reversion is deferred after equilibrium is reached.

In the above example, the water level is originally maintained at $L_1$ by using 2 m³ of water. In case the water level is maintained at $L_2$ by using 3 m³ of water and the sensor is set at $L_3$, 210 cm higher than $L_1$, the pressure exceeds the gauge pressure of 0.14 induced by 140 cm depth of the treating tank and it is no longer necessary to be concerned with the water depth in the treating tank. When the water level reaches $L_5$ and stirring starts, all of the 1 m³ of methane gas with gauge pressure of 0.21 to 0.49 atm is used for stirring.

Except for cases where the gas in the gas chamber 12 escapes from the stirring tower into the atmosphere without being used for stirring prior to detecting the water level because the amount of water is insufficient or the sensor is located too high, when the location of the sensor is raised while the water level remains constant, the pressure and amount of gas used for stirring increases in general and stirring intensity becomes high, while stirring frequency decreases. Conversely, when the location of the sensor is lowered, the pressure and amount of gas decreases and stirring intensity becomes low while stirring frequency increases.

When the location of the sensor remains constant and the amount of water is increased, while the maximum gas pressure used for stirring remains the same, gas volume decreases, stirring intensity is generally high, and stirring frequency increases. Conversely, when the amount of water is reduced, while the maximum gas pressure remains the same, the gas volume increases, stirring intensity is low in general and stirring frequency decreases.

Thus by changing either the location of the sensor or the amount of water in the water tank and the stirring tower, the pressure and volume of the stirring gas and the stirring frequency may be varied, which permits the optimal operation of the system depending on the amount of gas generating in the treating tank.

3. Cleaning and purification of Methane Gas

As explained in section "2. Automatic Gas-lift stirring Device" above, the methane gas generating in the treating tank 10 comes into contact with the water in the gas chamber 12 and the stirring tower 13, and it is also violently mixed with the water in the gas chamber 12 and the stirring tower 13 during stirring process before it reaches the bottom 17 of the treating tank 10, where it forms bubbles rising through the filter media set the water to be treated passing through the filter media, and finally flows into the gas tank 14 via outlet 16 and motor-driven valve 19.

Gas tank 14 is a water-sealed tank. The methane gas inlet pipe reaches the bottom of the tank, where the pipe end 32 branches out into a number of arms. Gushing gas forms bubbles rising up in the water and accumulates in the upper portion of the tank. Here again the methane gas is cleaned by the water.

Generally speaking, the gas generated from conventional methane gas generators is composed of 60–70% methane gas and 30–40% carbon dioxide. It may also contain a very small amount of hydrogen sulfide, depending on the kind of the organic substance to be treated. Therefore, although it is usable as fuel, it emits a slight odor during combustion and can be used only with a municipal gas combustion appliance.

The concentration of methane contained in the generated gas can be increased to 80–88% by the cleaning effect attained by passing the gas repeatedly into the water in the stirring process and in the gas tank, as mentioned above.

Of course, the concentration of methane varies depending on the kind and concentration of the organic substances to be treated, but the concentration of methane is approximately 20% higher (in other words, removing the corresponding concentration of carbon dioxide) than conventional methane gas generators. Therefore, the methane gas generated by this system emits no odor during combustion, and the calorie is remarkably higher than municipal gas and a combustion efficiency is close to that of natural gas.

The gas generating vigorously in the treating tank contains many viscous particles. It is therefore necessary to install strainers at strategic points to prevent blockage of narrow spaces in the system. The particles remaining after passing through the strainers can be most effectively removed through water-cleaning.

Figure 23:
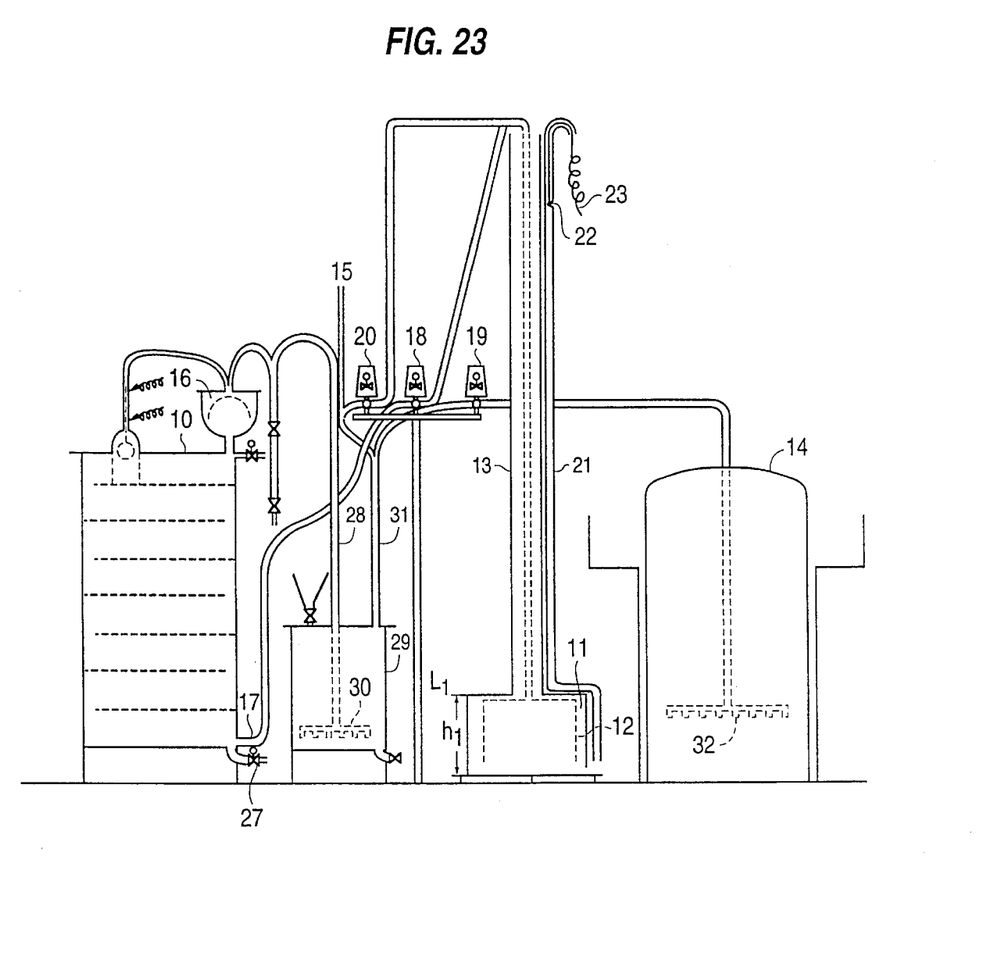
FIG. 23 is a diagrammatic view of an entire treating system comprising a horizontal zigzag flow tank, an automatic gas-lift stirring device, a gas tank and a methane gas cleaning and purifying apparatus.

FIG. 23 represents an embodiment of the system of this invention comprising a vertical zigzag flow tank, an automatic gas-lift stirring device and a cleaning and purifing device 29 for the generated gas.

Referring to FIG. 23, operation of the system is explained. The device 29 is filled with a saturated solution of calcium hydroxide $Ca(OH)_2$. Calcium hydroxide, or limewater, settles as calcium carbonate combining with carbon dioxide.

The methane gas generating in the treating tank 10 enters the cleaning and purifing device 29 through outlet 16 and inlet pipe 28. The end 30 of pipe 28 branches at the bottom of the device 29, and the gas forms numerous bubbles rising up in the device and enters the gas chamber through pipe 31 and motor-driven valve 20 which is open.

After that, the process is the same as that explained with reference to FIG. 19. Sensor 23 detects the water and close the valve 20 and open the valves 18 and 19. The gas entering the treating tank 10 via valve 18 and pipe 17 rises up from the bottom of the tank to the upper in a zigzag fashion along and between the partitions, which process naturally exerts a significant cleaning effect.

The rising gas is sent to the cleaning and purifying device 29 through the outlet 16 and passes through the limewater again, and thereafter enters the gas tank through the valve 19 and the branched holes 32 at the bottom and rises to the upper whereby the purification of the gas is made again.

Therefore, the installation of the device 29 adds a total of two gas-cleaning processes by the limewater, one occurring before and one after automatic gas-lift stirring. Replacing the water in the water tank 12 and the gas tank 14 with limewater will enhance the purification of the methane gas. The resulting gas will be closer to natural gas. An experiment has proven that hydrogen sulfide is also removed. The settlement, calcium carbonate or $CaCO_3$, can be reproduced and reused in the system. Mixing with a fertilizer enhances the effect of the fertilizer.

4. Filter Media

Figure 20:
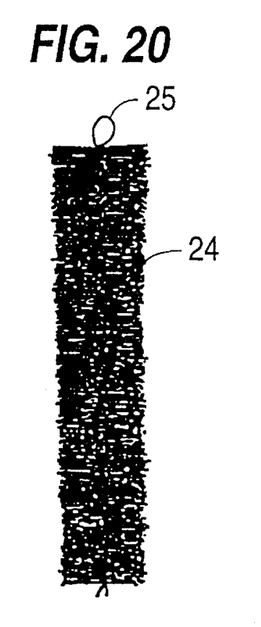
FIG. 20 is a front view showing one embodiment of filter medium to be installed in the treating tank.
Figure 21:
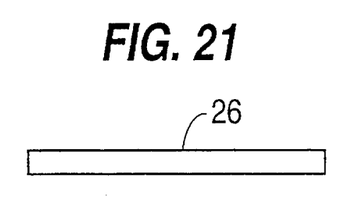
FIG. 21 is a front view of a tape element of the filter medium.
Figure 22:
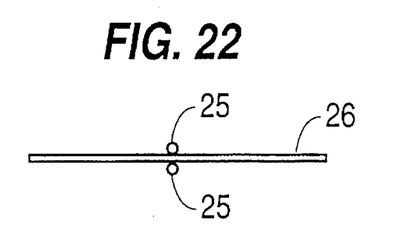
FIG. 22 is a diagrammatic view showing the relationship between a core element and a tape element of the filter medium.

Each chamber of the treating tank is filled with a filter medium 24 as shown in FIG. 20. A filter medium comprises a core element 25 and a number of thin tapes 26 made of synthetic resin extending radially around the core element. For example, the filter medium is made by aligning tapes 26 made of thin and wide synthetic resin film and cut to identical lengths of 30 to 60 cm, at the same close intervals, placing stainless steel core elements 25 on both sides of the tapes at the center portion, and twisting core elements 25. While the method of manufacture is the same as for stick brushes, the appearance looks like a duster for automobiles which are made of long ostrich tail feathers. The filter media 24 are installed so as to fill each chamber of the treating tank in either a standing or lying position.

In one method of installation, for example, a number of filter media are attached to a frame at both ends of the core element 25 and said assembly is placed in each the chambers. The filter media should be separated from each other at a distance such that the ends of the tapes 26 extending horizontally in the water to be treated slightly touch with those of adjacent tapes, because this degree of density permits easy operation and few breakdowns of the filter medium and also an effective treatment is obtainable.

Polypropylene is the best material for the filter medium. However, it is not necessary to limit to this material. Any material can be used as long as it has the same properties as polypropylene.

Polypropylene is obtainable stably and inexpensively. It is also light, with a specific gravity of 0.9. The tapes made of wide polypropylene films spread out straight to the end in the water to be treated. The material is very strong in physical property and also change of properties does not occur in water. No plasticizer being contained, toxic or organic substances are never eluted in water.

Further molecules being properly aligned lengthwise, the tape will not be severed transversely and shortened. In case strong shocks or vibrations are inflicted continuously over a long period of time, the tapes will simply split lengthwise into threads, and thereby the surface area is enlarged. Therefore, the more they are used, the more contact with bacteria they will have and the more sludge they will hold. As a result, the efficiency of methane fermentation is enhanced. Being entirely submerged in the water to be treated, the stainless steel core elements will not corrode.

The purpose of filling the treating tank with filter media or carriers is to hold as many reaction-causing anaerobic bacteria as possible by adhering the microbial membrane of the bacteria to the filter media or carriers. This principle applies to both the fixed-bed method and the fluidized bed method. With the fixed-bed method, however, the possibility of clogging is generally high, and therefore it is essential to deal with this problem.

The filter medium used in this invention may be classified as a fixed-bed method. However, in view of its shape and function, and further in relation with the aforementioned automatic gas-lift stirring, it goes without saying that it does not entail the problem of clogging. The microbial membrane adhered to the tapes which spread in the treating tank moves in all directions at varying speeds by the action of the methane gas gushing out from the holes at the bottom of the tank, it is closer to a fluidized bed than a fixed bed. Fluidized bed is necessary to maintain good fluidity and keep the buildup of microbial membrane relatively thin at all times. This requires the intake of organic substances and fluidity inside the tank through stirring. The filter media and the gas-lift stirring system in this invention are optimal to satisfy such requirements.

While it is generally said that the fluidized bed system is suitable for treatment of waste water having low concentrations of organic substances, this system can handle waste water of high, medium and low concentrations, because the aforementioned special filter media, as well as the ability to control the excess buildup of microbial membrane through the control of the volume and pressure of the gas and the frequency of stirring, ensure optimal conditions.

Although it is said that the fluidized bed system is high in the energy cost for creating fluidity in the treating tank, the automatic gas-lift stirring does not require any energy other than electric power for controlling the motor-driven valves because it utilizes the volume and pressure of gas generating in the treating tank.

5. Automatic Gas-Lift stirring Device and Filter Media

The microbial membranes adhered to the tapes 26 of the filter media move in all directions at varying speeds each time organic subtance is poured in and stirring takes place. As a result there occurs frequent and repeated collision between the membranes and the organic substances as being substrate, so that the treating efficiency is increased. However, if the microbial membranes are separated in large from the tapes by the shearing stress caused by the movement in the fluid and flowed out, treating efficiency drops remarkably.

Conversely, if the microbial membranes settle firmly onto the tapes and begin to grow larger, it is said that the substrate penetrates into the inside of the membrane through molecular diffusion because there is no flow of fluid in the membrane and that there occurs a distribution of the substrate in the microbial membranes when the substrate is consumed by the microorganism in the diffusion process so that the treating efficiency decreases.

When the microbial membranes are separated in large, it takes a considerable length of time for recovering because the membranes are created very slowly. Therefore, it is required that the separation is controlled not so as to form surplus microbial membranes so that the concentration of bacteria in the treating tank is maintained high at all times for a long period of time.

Control of membrane thickness has conventionally been performed by mechanical stirring or pumps, but it requires high skills and long experience and is still ambiguous. Recent microbiological research on anaerobic treatment has progressed greatly and enormous reports have been presented. Nevertheless, no method to measure the bacteria for the anaerobic treatment has been discovered. Even high-efficiency methane fermentation methods are not designed based on the metabolic or biological features of acid-generating bacteria and methane-generating bacteria, nor has any manipulation of such a nature been performed. Search and developments have been directed exclusively to maintain as many anaerobic bacteria as possible in the treating tank. Accordingly treatment is limited to specific organic substances having high concentrations.

In order to treat organic substances of various kinds and of a wide range of concentrations, this invention provides the treatment tank of a horizontal zigzag flow, vertical zigzag flow or vertical alternate flow type, and at the same time, utilizes the generally-known fact that the degree of activity of methane-generating bacteria increases in proportion to the amount of methane gas generated. Of course such exceptions are excluded as that gas generation temporarily increases immediately after an excessive load is subjected accompanying the increase of the proportion of carbon dioxide and thereafter the activity of methane-generating bacteria and gas generation decreases significantly. When a certain amount of methane gas generated at a certain degree of activity of the methane-generating bacteria is used for stirring at a given pressure and frequency, the collision frequency between the microorganism and the organic substances increases, and the gas generation and the frequency of gas-lift stirring under the same gas volume and pressure increases. The methane-generating bacteria then become even more active and the gas generation and stirring frequency increases.

When the intensity (gas volume and pressure) and frequency of stirring exceeds a certain limit, separation of the microbial membranes increases and thereby the gas generation decreases. It is too late to alter the operation of the system after such decrease occurs, and restoration of the membranes will take a long time. In the gas-lift stirring in this invention, however, the gas generation decreases immediately after a peak is reached. Accordingly stirring frequency is reduced and the separation is controlled and thus automatic control is attained so as to maintain optimal gas generation by stirring with a prescribed gas volume and pressure. This maintains the activity of the methane-generating bacteria in the treating tank and keeps gas generation at the maximum level under the preset conditions. In the operation of this system, the maximum gas volume (gas volume× gas pressure× stirring frequency) should be obtained by taking into consideration the nature, concentration and volume of the organic substances to be treated and changing the volume of water to be poured into the water tank and the stirring tower, as well as the location of the sensor, to ensure optimal efficiency in the treatment of the organic substance in the treating tank at that time.

6. Collecting and Removing Device for Scum and Sludge

Since the vertical alternate flow system performs alternate upward flow and downward flow and said flows are changeable via connecting tubes, there is no need to remove the scum which could accumulate in the upper portion of the treating tank and accumulation of sludge at the tank bottom can be prevented as well. But in the case of the horizontal zigzag flow system, there is a possibility that scum accumulates in the upper portion and sludge accumulates in the lowest portion of the tank.

Therefore, either inside or outside the tank wall, there is installed a jacket having a sloped bottom and an open top which is connected to the inside of the tank. Overflowing scum is collected in this jacket and removed through a pipe connected to it at the lowest end of the slope. Thus the scum can be effectively removed.

For removal of sludges contained in the waste water, it may be effective to install a sludge tank. Said sludge tank is connected via a valve to the lowest portion of the treating tank bottom. A float is provided in the sludge tank for detecting the surface of the liquid and closing the valve automatically when a certain amount of sludge has flowed into the sludge tank. The sludge in the sludge tank is sent back to the treating tank via a pump according to a predetermined cycle. In FIGS. 2 and 4, the connecting outlet to the sludge tank is indicated by numeral 27.

INDUSTRIAL APPLICABILITY

As explained above in detail, the treating system of this invention improves filter media, treating tank and automatic gas-lift stirring in the tank, and provides the best system for the anaerobic treatment of organic solid and liquid waste. Accordingly the present system has various advantages over conventional systems of the same nature, e.g. wide applicability of various organic substances, high treatment efficiency, low installing and running costs, and easy operation.

An anaerobic treatment system utilizing the vertical alternate flow tank permits the repair, renovation and suspension of operation of a part of the tank without stopping the operation of the whole system just by changing the connections of the connecting tubes. It also permits the conversion of a part or all of the tank into a separation or seeding tank, or even into an aerobic tank or a mere anaerobic filter bed, while retaining high treatment efficiency.

It is also advantageous in that if the chambers are mass-produced as standarized components, reduction of costs and easy transportation can be attained and further a wide selection can be made for the location of installation. One of the chambers can be used as a seeding tank to maintain in a hungry state a number of the same methane-generating bacteria, which enables to cope with the great change in the organic substances and the load. When seasonal fresh products or fruits are processed into secondary products, organic substances to be treated yields temporarily but in a great deal. Easy transportation of the system and full applicability of the methane —generating bacteria maintained in the seeding tank enables the optimal treatment of the above organic substances.

Methane fermentation treatment systems have been seen in many places for the treatment of livestock waste. However, in spite of the fact that farm owners obtained subsidies for the installation of these treatment systems, they were closed down in a few years because of their high operating and repairing costs. Since the system of this invention has few mechanical parts and receives and discharges organic substances with only a single pump, installation, running and repairing costs are low. In case the assembly-type system is operated or two or three sets of the horizontal zigzag flow system or the vertical zigzag flow system are operated simultaneously, no breakage will occur for a long period of time as regular maintenance and repairs can be made on individual units without stopping the whole operation.

The treated or fermented solution generating after methane fermentation treatment can be used for the manufacture of conventional compost. If appropriately diluted by water, it can also be used as an organic fertilizer having an immediate effect.

I claim:

1. A treating system for organic solid and liquid waste comprising:
   (a) a horizontal zigzag flow treating tank having a sloped bottom and a plurality of chambers defined within the tank by horizontally dividing the interior of the tank with partitions disposed in a zigzag fashion with each partition having an orientation different from an adjacent partition and connected to one another in a horizontal zigzag fashion;
   (b) filter media for holding bacteria installed in each chamber in a standing position, said filter media being composed of a core element and multiple thin tapes of synthetic resin extending radially around the core element so that said tapes float in liquid waste to be treated with the ends of said tapes slightly touching adjacent tapes; and
   (c) an automatic gas-lift stirring device having a gas chamber connected through valves to a methane gas outlet provided at the top of the tank and to a methane gas inlet at the bottom of the tank, said automatic gas-lift stirring device including:
      a water tank for holding a prescribed amount of liquid, a stirring tower of a cylindrical shape with an open top connected to the top of said water tank,
      a gas chamber provided in said water tank and having an open bottom through which the gas chamber is connected to the inside of the water tank and the stirring tower, and
      detecting means which generates control signals to close a valve to the methane gas outlet and open a valve to the methane gas inlet when detecting a prescribed upper level of the liquid rising in said stirring tower due to gas pressure in the gas chamber,
   said treating tank receiving waste to be treated at the upper side of the slope and discharging treated substances from the lower side of the slope.

2. A treating system for organic solid and liquid waste comprising:
   (a) a vertical zigzag flow treating tank having a plurality of chambers defined within the tank by vertically dividing the interior of the tank with partitions disposed horizontally and extended in opposite directions in turn from an inner wall of the tank with an aperture formed at the end of each partition to connect each chamber in a vertical zigzag fashion wherein treating substances flow parallel to the partitions;
   (b) filter media for holding bacteria installed in each chamber in a lying position, said filter media being composed of a core element and multiple thin tapes of synthetic resin extending radially around the core element so that said tapes float in liquid waste to be treated with the ends of said tapes slightly touching adjacent tapes; and
   (c) an automatic gas-lift stirring device having a gas chamber connected through valves to a methane gas outlet provided at the top of the tank and to a methane gas inlet at the bottom of the tank, said automatic gas-lift stirring device including:
      a water tank for holding a prescribed amount of liquid, a stirring tower of a cylindrical shape with an open top connected to the top of said water tank,
      a gas chamber provided in said water tank and having an open bottom through which the gas chamber is connected to the inside of the water tank and the stirring tower, and
      detecting means which generates control signals to close a valve to the methane gas outlet and open a valve to the methane gas inlet when detecting a prescribed upper level of the liquid rising in said stirring tower due to gas pressure in the gas chamber,
   said treating tank receiving waste to be treated at either a top or bottom end and discharging treated substances from the other end.

3. A treating system for organic solid and liquid water comprising:
   (a) a vertical alternate flow treating tank having independent chambers connected to one another by connecting tubes wherein treating substances flow in an alternating fashion of upward and downward flows and are discharged from a final chamber;
   (b) filter media for holding bacteria installed in each chamber in a standing position, said filter media being composed of a core element and multiple thin tapes of synthetic resin extending radially around the core element so that said tapes float in liquid waste to be treated with the ends of said tapes slightly touching adjacent tapes; and (c) an automatic gas-lift stirring device having a gas chamber connected through valves to a methane gas outlet provided at the top of the tank and to a methane gas inlet at the bottom of the tank, said automatic gas-lift stirring device including:

a water tank for holding a prescribed amount of liquid,
a stirring tower of a cylindrical shape with an open top connected to the top of said water tank,
a gas chamber provided in said water tank and having an open bottom through which the gas chamber is connected to the inside of the water tank and the stirring tower, and detecting means which generates control signals to close a valve to the methane gas outlet and open a valve to the methane gas inlet when detecting a prescribed upper level of the liquid rising in said stirring tower due to gas pressure in the gas chamber.

* * * * *